(12) United States Patent  
Guo et al.

(10) Patent No.: US 8,722,382 B1
(45) Date of Patent: May 13, 2014

(54) XYLANASE HAVING IMPROVED ENZYMATIC ACTIVITY

(71) Applicant: Dongguan APAC Biotechnology Co., Ltd., DongGuan (CN)

(72) Inventors: Rey-Ting Guo, Taipei (TW); Ya-Shan Cheng, Taipei (TW); Jian-Wen Huang, Taipei (TW); Tzu-Hui Wu, Taipei (TW); Hui-Lin Lai, Taipei (TW); Cheng-Yen Lin, Taipei (TW); Ting-Yung Huang, Taipei (TW)

(73) Assignee: Dongguan APAC Biotechnology Co., Ltd., DongGuan (CN)

( * ) Notice: Subject to any disclaimer, the term of this patent is extended or adjusted under 35 U.S.C. 154(b) by 0 days.

(21) Appl. No.: 14/039,017

(22) Filed: Sep. 27, 2013

(30) Foreign Application Priority Data

Apr. 17, 2013 (TW) .............................. 102113687 U

(51) Int. Cl.
*C12N 9/42* (2006.01)

(52) U.S. Cl.
USPC ..... 435/209; 435/254.3; 435/69.1; 435/254.2

(58) Field of Classification Search
USPC .......... 435/209, 277, 263, 254.2, 254.3, 69.1, 435/440, 41, 161, 165; 536/23.2, 23.74; 510/320; 426/442, 11, 31; 162/72, 5; 8/401; 502/7
See application file for complete search history.

(56) References Cited

PUBLICATIONS

Jin Ho et al (Characterization of a *Neocallimastix patriciarum* xylanase gene and its product Canadian Journal of Microbiology Nov. 1999 45(11):970-974.*

* cited by examiner

*Primary Examiner* — Kagnew H Gebreyesus
(74) *Attorney, Agent, or Firm* — Kirton McConkie; Evan R. Witt

(57) ABSTRACT

A xylanase having increased enzymaic activity is disclosed. The xylanase has a modified amino acid sequence of SEQ ID NO: 2, wherein Tryptophan at position 125 is substituted with Phenylalanine and Phenylalanine at position 163 is substituted with Tryptophan.

10 Claims, 4 Drawing Sheets

```
cagtccttctgttcttctgcttcccactctggtcagtccgttaaggttactggtaacaaggttggtactatcggtggtgttggttacgaa
 Q  S  F  C  S  S  A  S  H  S  G  Q  S  V  K  V  T  G  N  K  V  G  T  I  G  G  V  G  Y  E ttgtgggctgattccggtaacaactccgctactttctactctgacggttccttctcctgtactttccaaaacgctggtgactacttgtgt
 L  W  A  D  S  G  N  N  S  A  T  F  Y  S  D  G  S  F  S  C  T  F  Q  N  A  G  D  Y  L  C agatccggtttgtctttcgactccactaagactccatcccagatcggtagaatgaaggctgacttcaagttggttaagcagaactcctct
 R  S  G  L  S  F  D  S  T  K  T  P  S  Q  I  G  R  M  K  A  D  F  K  L  V  K  Q  N  S  S aacgttggttactcctacgttggtgtttacggttggactagatccccattggttgagtactacatcgttgacaactggttgtccccattc
 N  V  G  Y  S  Y  V  G  V  Y  G  W  T  R  S  P  L  V  E  Y  Y  I  V  D  N  W  L  S  P  F ccaccaggtgattgggttggtaacaaaaagcacggatccttcactatcgacggtgctcagtacactgtttacgagaacactagaactggt
 P  P  G  D  W  V  G  N  K  K  H  G  S  F  T  I  D  G  A  Q  Y  T  V  Y  E  N  T  R  T  G ccatccattgacggtgacactactttcaaccagtacttctccatcagacagcaggctagagactgtggaactattgacatttccgctcac
 P  S  I  D  G  D  T  T  F  N  Q  Y  F  S  I  R  Q  Q  A  R  D  C  G  T  I  D  I  S  A  H ttcgaccagtgggagaagttgggtatgactatgggaaagttgcacgaggctaaggttttggtgaagctggtaacgttaacggtggtgct
 F  D  Q  W  E  K  L  G  M  T  M  G  K  L  H  E  A  K  V  L  G  E  A  G  N  V  N  G  A tctggtactgctgatttcccatacgctaaagtttacatcggtgattaa  -SEQ ID NO: 1
 S  G  T  A  D  F  P  Y  A  K  V  Y  I  G  D  *   -SEQ ID NO: 2
```

FIG. 1

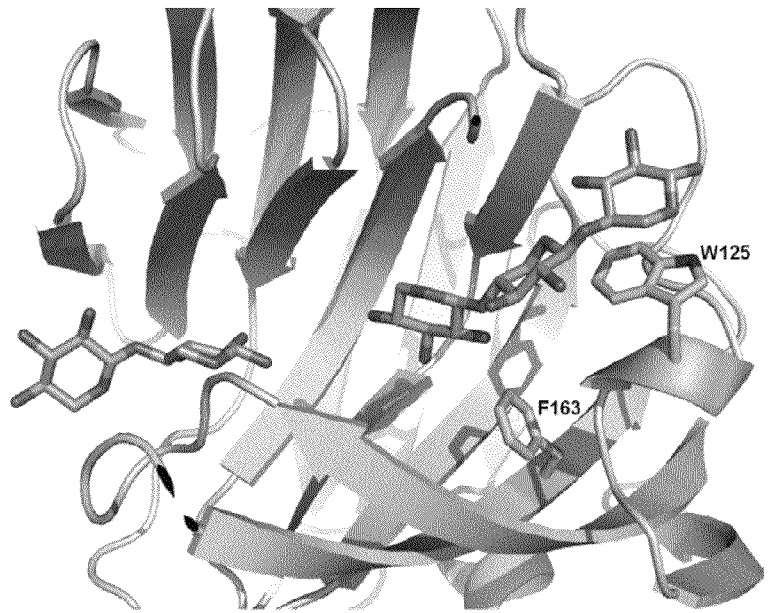

FIG. 2

| Mutants | Sequences of mutagenic primers |
|---|---|
| W125F | 5'- CCATTCCCACCAGGTGATTTTGTTGGTAACAAAAAGCAC -3' |
| F163W | 5'- ACTACTTTCAACCAGTACTGGTCCATCAGACAGCAGGCT -3' |

FIG. 3

```
cagtccttctgttcttctgcttcccactctggtcagtccgttaaggttactggtaacaaggttggtactatcggtggtgttggttacgaa
 Q  S  F  C  S  S  A  S  H  S  G  Q  S  V  K  V  T  G  N  K  V  G  T  I  G  G  V  G  Y  E ttgtgggctgattccggtaacaactccgctactttctactctgacggttccttctctgtactttccaaaacgctggtgactacttgtgt
 L  W  A  D  S  G  N  N  S  A  T  F  Y  S  D  G  S  F  S  C  T  F  Q  N  A  G  D  Y  L  C agatccggtttgtctttcgactccactaagactccatcccagatcggtagaatgaaggctgacttcaagttggttaagcagaactcctct
 R  S  G  L  S  F  D  S  T  K  T  P  S  Q  I  G  R  M  K  A  D  F  K  L  V  K  Q  N  S  S aacgttggttactcctacgttggtgtttacggttggactagatccccattggttgagtactacatcgttgacaactggttgtcccattc
 N  V  G  Y  S  Y  V  G  V  Y  G  W  T  R  S  P  L  V  E  Y  Y  I  V  D  N  W  L  S  P  F ccaccaggtgatttttgttggtaacaaaaagcacggatccttcactatcgacggtgctcagtacactgtttacgagaacactagaactggt
 P  P  G  D  F  V  G  N  K  K  H  G  S  F  T  I  D  G  A  Q  Y  T  V  Y  E  N  T  R  T  G ccatccattgacggtgacactacttt caaccagtacttctccatcagacagcaggctagagactgtggaactattgacatttccgctcac
 P  S  I  D  G  D  T  T  F  N  Q  Y  F  S  I  R  Q  Q  A  R  D  C  G  T  I  D  I  S  A  H ttcgaccagtgggagaagttgggtatgactatgggaaagttgcacgaggctaaggttttgggtgaagctggtaacgttaacggtggtgct
 F  D  Q  W  E  K  L  G  M  T  M  G  K  L  H  E  A  K  V  L  G  E  A  G  N  V  N  G  G  A tctggtactgctgatttcccatacgctaaagtttacatcggtgattaa   -SEQ ID NO: 3
 S  G  T  A  D  F  P  Y  A  K  V  Y  I  G  D  *    -SEQ ID NO: 4
```

FIG. 4

```
cagtccttctgttcttctgcttcccactctggtcagtccgttaaggttactggtaacaaggttggtactatcggtggtgttggttacgaa
 Q   S   F   C   S   S   A   S   H   S   G   Q   S   V   K   V   T   G   N   K   V   G   T   I   G   G   V   G   Y   E ttgtgggctgattccggtaacaactccgctactttctactctgacggttccttctcctgtacttccaaaacgctggtgactacttgtgt
 L   W   A   D   S   G   N   N   S   A   T   F   Y   S   D   G   S   F   S   C   T   F   Q   N   A   G   D   Y   L   C agatccggtttgtctttcgactccactaagactccatcccagatcggtagaatgaaggctgacttcaagttggttaagcagaactcctct
 R   S   G   L   S   F   D   S   T   K   T   P   S   Q   I   G   R   M   K   A   D   F   K   L   V   K   Q   N   S   S aacgttggttactcctacgttggtgtttacggttggactagatccccattggttgagtactacatcgttgacaactggttgtccccattc
 N   V   G   Y   S   Y   V   G   V   Y   G   W   T   R   S   P   L   V   E   Y   Y   I   V   D   N   W   L   S   P   F ccaccaggtgattgggttggtaacaaaaagcacggatccttcactatcgacggtgctcagtacactgtttacgagaacactagaactggt
 P   P   G   D   W   V   G   N   K   K   H   G   S   F   T   I   D   G   A   Q   Y   T   V   Y   E   N   T   R   T   G ccatccattgacggtgacactactttcaaccagtac[tgg]ccatcagacagcaggctagagactgtggaactattgacatttccgctcac
 P   S   I   D   G   D   T   T   F   N   Q   Y  [W]  S   I   R   Q   Q   A   R   D   C   G   T   I   D   I   S   A   H ttcgaccagtgggagaagttgggtatgactatgggaaagttgcacgaggctaaggttttgggtgaagctggtaacgttaacggtggtgct
 F   D   Q   W   E   K   L   G   M   T   M   G   K   L   H   E   A   K   V   L   G   E   A   G   N   V   N   G   G   A tctggtactgctgatttcccatacgctaaagtttacatcggtgattaa  -SEQ ID NO: 5
 S   G   T   A   D   F   P   Y   A   K   V   Y   I   G   D   *    -SEQ ID NO: 6
```

FIG. 5

```
cagtccttctgttcttctgcttcccactctggtcagtccgttaaggttactggtaacaaggttggtactatcggtggtgttggttacgaa
 Q   S   F   C   S   S   A   S   H   S   G   Q   S   V   K   V   T   G   N   K   V   G   T   I   G   G   V   G   Y   E ttgtgggctgattccggtaacaactccgctactttctactctgacggttccttctcctgtacttccaaaacgctggtgactacttgtgt
 L   W   A   D   S   G   N   N   S   A   T   F   Y   S   D   G   S   F   S   C   T   F   Q   N   A   G   D   Y   L   C agatccggtttgtctttcgactccactaagactccatcccagatcggtagaatgaaggctgacttcaagttggttaagcagaactcctct
 R   S   G   L   S   F   D   S   T   K   T   P   S   Q   I   G   R   M   K   A   D   F   K   L   V   K   Q   N   S   S aacgttggttactcctacgttggtgtttacggttggactagatccccattggttgagtactacatcgttgacaactggttgtccccattc
 N   V   G   Y   S   Y   V   G   V   Y   G   W   T   R   S   P   L   V   E   Y   Y   I   V   D   N   W   L   S   P   F ccaccaggtga[ttt]gttggtaacaaaaagcacggatccttcactatcgacggtgctcagtacactgtttacgagaacactagaactggt
 P   P   G   D  [F]  V   G   N   K   K   H   G   S   F   T   I   D   G   A   Q   Y   T   V   Y   E   N   T   R   T   G ccatccattgacggtgacactactttcaaccagtac[tgg]ccatcagacagcaggctagagactgtggaactattgacatttccgctcac
 P   S   I   D   G   D   T   T   F   N   Q   Y  [W]  S   I   R   Q   Q   A   R   D   C   G   T   I   D   I   S   A   H ttcgaccagtgggagaagttgggtatgactatgggaaagttgcacgaggctaaggttttgggtgaagctggtaacgttaacggtggtgct
 F   D   Q   W   E   K   L   G   M   T   M   G   K   L   H   E   A   K   V   L   G   E   A   G   N   V   N   G   G   A tctggtactgctgatttcccatacgctaaagtttacatcggtgattaa  -SEQ ID NO: 7
 S   G   T   A   D   F   P   Y   A   K   V   Y   I   G   D   *    -SEQ ID NO: 8
```

FIG. 6

SEQUENCE LISTING

<160> NUMBER OF SEQ ID NOS: 8

<210> SEQ ID NO 1
<211> LENGTH: 678
<212> TYPE: DNA
<213> ORGANISM: Neocallimastix patriciarum

<400> SEQUENCE: 1

```
cagtccttct gttcttctgc ttcccactct ggtcagtccg ttaaggttac tggtaacaag      60
gttggtacta tcggtggtgt tggttacgaa ttgtgggctg attccggtaa caactccgct     120
actttctact ctgacggttc cttctcctgt actttccaaa acgctggtga ctacttgtgt     180
agatccggtt tgtctttcga ctccactaag actccatccc agatcggtag aatgaaggct     240
gacttcaagt tggttaagca gaactcctct aacgttggtt actcctacgt tggtgtttac     300
ggttggacta gatccccatt ggttgagtac tacatcgttg acaactggtt gtccccattc     360
ccaccaggtg attgggttgg taacaaaaag cacggatcct tcactatcga cggtgctcag     420
tacactgttt acgagaacac tagaactggt ccatccattg acggtgacac tactttcaac     480
cagtacttct ccatcagaca gcaggctaga gactgtggaa ctattgacat tccgctcac      540 ttcgaccagt gggagaagtt gggtatgact atgggaaagt tgcacgaggc taaggttttg     600
ggtgaagctg gtaacgttaa cggtggtgct tctggtactg ctgatttccc atacgctaaa     660
gtttacatcg gtgattaa                                                   678
```

<210> SEQ ID NO 2
<211> LENGTH: 225
<212> TYPE: PRT
<213> ORGANISM: Neocallimastix patriciarum

<400> SEQUENCE: 2

```
Gln Ser Phe Cys Ser Ser Ala Ser His Ser Gly Gln Ser Val Lys Val
 1               5                  10                  15

Thr Gly Asn Lys Val Gly Thr Ile Gly Gly Val Gly Tyr Glu Leu Trp
                20                  25                  30

Ala Asp Ser Gly Asn Asn Ser Ala Thr Phe Tyr Ser Asp Gly Ser Phe
            35                  40                  45

Ser Cys Thr Phe Gln Asn Ala Gly Asp Tyr Leu Cys Arg Ser Gly Leu
        50                  55                  60

Ser Phe Asp Ser Thr Lys Thr Pro Ser Gln Ile Gly Arg Met Lys Ala
65                  70                  75                  80
```

Asp Phe Lys Leu Val Lys Gln Asn Ser Ser Asn Val Gly Tyr Ser Tyr
            85                  90                  95

Val Gly Val Tyr Gly Trp Thr Arg Ser Pro Leu Val Glu Tyr Tyr Ile
        100                 105                 110

Val Asp Asn Trp Leu Ser Pro Phe Pro Gly Asp Trp Val Gly Asn
            115                 120                 125

Lys Lys His Gly Ser Phe Thr Ile Asp Gly Ala Gln Tyr Thr Val Tyr
    130                 135                 140

Glu Asn Thr Arg Thr Gly Pro Ser Ile Asp Gly Asp Thr Thr Phe Asn
145                 150                 155                 160

Gln Tyr Phe Ser Ile Arg Gln Gln Ala Arg Asp Cys Gly Thr Ile Asp
                165                 170                 175

Ile Ser Ala His Phe Asp Gln Trp Glu Lys Leu Gly Met Thr Met Gly
            180                 185                 190

Lys Leu His Glu Ala Lys Val Leu Gly Glu Ala Gly Asn Val Asn Gly
        195                 200                 205

Gly Ala Ser Gly Thr Ala Asp Phe Pro Tyr Ala Lys Val Tyr Ile Gly
    210                 215                 220

Asp
225

<210> SEQ ID NO 3
<211> LENGTH: 678
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 3
cagtccttct gttcttctgc ttcccactct ggtcagtccg ttaaggttac tggtaacaag      60
gttggtacta tcggtggtgt tggttacgaa ttgtgggctg attccggtaa caactccgct     120
actttctact ctgacggttc cttctcctgt actttccaaa acgctggtga ctacttgtgt     180
agatccggtt tgtctttcga ctccactaag actccatccc agatcggtag aatgaaggct     240
gacttcaagt tggttaagca gaactcctct aacgttggtt actcctacgt tggtgtttac     300
ggttggacta gatccccatt ggttgagtac tacatcgttg acaactggtt gtccccattc     360
ccaccaggtg attttgttgg taacaaaaag cacggatcct tcactatcga cggtgctcag     420
tacactgttt acgagaacac tagaactggt ccatccattg acggtgacac tacttcaac      480 cagtacttct ccatcagaca gcaggctaga gactgtggaa ctattgacat tccgctcac      540 ttcgaccagt gggagaagtt gggtatgact atgggaaagt tgcacgaggc taaggttttg     600
ggtgaagctg gtaacgttaa cggtggtgct tctggtactg ctgatttccc atacgctaaa     660
gtttacatcg gtgattaa                                                    678

<210> SEQ ID NO 4
<211> LENGTH: 225
<212> TYPE: PRT
<213> ORGANISM: Artificial Sequence
<220> FEATURE:
<223> OTHER INFORMATION: Sequence synthetically translated from SEQ ID
      NO: 3

<400> SEQUENCE: 4

Gln Ser Phe Cys Ser Ser Ala Ser His Ser Gly Gln Ser Val Lys Val
1               5                   10                  15

```
Thr Gly Asn Lys Val Gly Thr Ile Gly Gly Val Gly Tyr Glu Leu Trp
         20                  25                  30
Ala Asp Ser Gly Asn Asn Ser Ala Thr Phe Tyr Ser Asp Gly Ser Phe
             35                  40                  45
Ser Cys Thr Phe Gln Asn Ala Gly Asp Tyr Leu Cys Arg Ser Gly Leu
 50                  55                  60
Ser Phe Asp Ser Thr Lys Thr Pro Ser Gln Ile Gly Arg Met Lys Ala
 65                  70                  75                  80
Asp Phe Lys Leu Val Lys Gln Asn Ser Ser Asn Val Gly Tyr Ser Tyr
                 85                  90                  95
Val Gly Val Tyr Gly Trp Thr Arg Ser Pro Leu Val Glu Tyr Tyr Ile
                100                 105                 110
Val Asp Asn Trp Leu Ser Pro Phe Pro Pro Gly Asp Phe Val Gly Asn
             115                 120                 125
Lys Lys His Gly Ser Phe Thr Ile Asp Gly Ala Gln Tyr Thr Val Tyr
        130                 135                 140
Glu Asn Thr Arg Thr Gly Pro Ser Ile Asp Gly Asp Thr Thr Phe Asn
145                 150                 155                 160
Gln Tyr Phe Ser Ile Arg Gln Gln Ala Arg Asp Cys Gly Thr Ile Asp
                165                 170                 175
Ile Ser Ala His Phe Asp Gln Trp Glu Lys Leu Gly Met Thr Met Gly
             180                 185                 190
Lys Leu His Glu Ala Lys Val Leu Gly Glu Ala Gly Asn Val Asn Gly
        195                 200                 205
Gly Ala Ser Gly Thr Ala Asp Phe Pro Tyr Ala Lys Val Tyr Ile Gly
    210                 215                 220
Asp
225

<210> SEQ ID NO 5
<211> LENGTH: 678
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 5
cagtccttct gttcttctgc ttcccactct ggtcagtccg ttaaggttac tggtaacaag      60
gttggtacta tcggtggtgt tggttacgaa ttgtgggctg attccggtaa caactccgct     120
actttctact ctgacggttc cttctcctgt actttccaaa acgctggtga ctacttgtgt     180
agatccggtt tgtctttcga ctccactaag actccatccc agatcggtag aatgaaggct     240
gacttcaagt tggttaagca gaactcctct aacgttggtt actcctacgt tggtgtttac     300
ggttggacta atcccccatt ggttgagtac tacatcgttg acaactggtt gtccccattc     360
ccaccaggtg attgggttgg taacaaaaag cacggatcct tcactatcga cggtgctcag     420
tacactgttt acgagaacac tagaactggt ccatccattg acggtgacac tactttcaac     480
cagtactggt ccatcagaca gcaggctaga gactgtggaa ctattgacat ttccgctcac     540
ttcgaccagt gggagaagtt gggtatgact atgggaaagt tgcacgaggc taaggttttg     600
ggtgaagctg gtaacgttaa cggtggtgct tctggtactg ctgatttccc atacgctaaa     660
gtttacatcg gtgattaa                                                   678

<210> SEQ ID NO 6
<211> LENGTH: 225
```

```
<212> TYPE: PRT
<213> ORGANISM: Artificial Sequence
<220> FEATURE:
<223> OTHER INFORMATION: Sequence synthetically translated from SEQ ID
      NO: 5

<400> SEQUENCE: 6

Gln Ser Phe Cys Ser Ser Ala Ser His Ser Gly Gln Ser Val Lys Val
 1               5                  10                  15

Thr Gly Asn Lys Val Gly Thr Ile Gly Gly Val Gly Tyr Glu Leu Trp
             20                  25                  30

Ala Asp Ser Gly Asn Asn Ser Ala Thr Phe Tyr Ser Asp Gly Ser Phe
         35                  40                  45

Ser Cys Thr Phe Gln Asn Ala Gly Asp Tyr Leu Cys Arg Ser Gly Leu
     50                  55                  60

Ser Phe Asp Ser Thr Lys Thr Pro Ser Gln Ile Gly Arg Met Lys Ala
 65                  70                  75                  80

Asp Phe Lys Leu Val Lys Gln Asn Ser Ser Asn Val Gly Tyr Ser Tyr
                 85                  90                  95

Val Gly Val Tyr Gly Trp Thr Arg Ser Pro Leu Val Glu Tyr Tyr Ile
            100                 105                 110

Val Asp Asn Trp Leu Ser Pro Phe Pro Pro Gly Asp Trp Val Gly Asn
        115                 120                 125

Lys Lys His Gly Ser Phe Thr Ile Asp Gly Ala Gln Tyr Thr Val Tyr
    130                 135                 140

Glu Asn Thr Arg Thr Gly Pro Ser Ile Asp Gly Asp Thr Thr Phe Asn
145                 150                 155                 160

Gln Tyr Trp Ser Ile Arg Gln Gln Ala Arg Asp Cys Gly Thr Ile Asp
                165                 170                 175

Ile Ser Ala His Phe Asp Gln Trp Glu Lys Leu Gly Met Thr Met Gly
            180                 185                 190

Lys Leu His Glu Ala Lys Val Leu Gly Glu Ala Gly Asn Val Asn Gly
        195                 200                 205

Gly Ala Ser Gly Thr Ala Asp Phe Pro Tyr Ala Lys Val Tyr Ile Gly
    210                 215                 220

Asp
225

<210> SEQ ID NO 7
<211> LENGTH: 678
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 7
cagtccttct gttcttctgc ttcccactct ggtcagtccg ttaaggttac tggtaacaag      60
gttggtacta tcggtggtgt tggttacgaa ttgtgggctg attccggtaa caactccgct     120
actttctact ctgacggttc cttctcctgt actttccaaa acgctggtga ctacttgtgt     180
agatccggtt tgtctttcga ctccactaag actccatccc agatcggtag aatgaaggct     240
gacttcaagt tggttaagca gaactcctct aacgttggtt actcctacgt tggtgtttac     300
ggttggacta gatccccatt ggttgagtac tacatcgttg acaactggtt gtccccattc     360
ccaccaggtg attttgttgg taacaaaaag cacggatcct tcactatcga cggtgctcag     420
tacactgttt acgagaacac tagaactggt ccatccattg acggtgacac tactttcaac     480
```

```
cagtactggt ccatcagaca gcaggctaga gactgtggaa ctattgacat ttccgctcac    540
ttcgaccagt gggagaagtt gggtatgact atgggaaagt tgcacgaggc taaggttttg    600
ggtgaagctg gtaacgttaa cggtggtgct tctggtactg ctgatttccc atacgctaaa    660
gtttacatcg gtgattaa                                                  678

<210> SEQ ID NO 8
<211> LENGTH: 225
<212> TYPE: PRT
<213> ORGANISM: Artificial Sequence
<220> FEATURE:
<223> OTHER INFORMATION: Sequence synthetically translated from SEQ ID
      NO: 7

<400> SEQUENCE: 8

Gln Ser Phe Cys Ser Ser Ala Ser His Ser Gly Gln Ser Val Lys Val
 1               5                  10                  15

Thr Gly Asn Lys Val Gly Thr Ile Gly Gly Val Gly Tyr Glu Leu Trp
            20                  25                  30

Ala Asp Ser Gly Asn Asn Ser Ala Thr Phe Tyr Ser Asp Gly Ser Phe
        35                  40                  45

Ser Cys Thr Phe Gln Asn Ala Gly Asp Tyr Leu Cys Arg Ser Gly Leu
    50                  55                  60

Ser Phe Asp Ser Thr Lys Thr Pro Ser Gln Ile Gly Arg Met Lys Ala
65                  70                  75                  80

Asp Phe Lys Leu Val Lys Gln Asn Ser Ser Asn Val Gly Tyr Ser Tyr
                85                  90                  95

Val Gly Val Tyr Gly Trp Thr Arg Ser Pro Leu Val Glu Tyr Tyr Ile
            100                 105                 110

Val Asp Asn Trp Leu Ser Pro Phe Pro Pro Gly Asp Phe Val Gly Asn
        115                 120                 125

Lys Lys His Gly Ser Phe Thr Ile Asp Gly Ala Gln Tyr Thr Val Tyr
    130                 135                 140

Glu Asn Thr Arg Thr Gly Pro Ser Ile Asp Gly Asp Thr Thr Phe Asn
145                 150                 155                 160

Gln Tyr Trp Ser Ile Arg Gln Gln Ala Arg Asp Cys Gly Thr Ile Asp
                165                 170                 175

Ile Ser Ala His Phe Asp Gln Trp Glu Lys Leu Gly Met Thr Met Gly
            180                 185                 190

Lys Leu His Glu Ala Lys Val Leu Gly Glu Ala Gly Asn Val Asn Gly
    195                 200                 205

Gly Ala Ser Gly Thr Ala Asp Phe Pro Tyr Ala Lys Val Tyr Ile Gly
    210                 215                 220

Asp
225
```

XYLANASE HAVING IMPROVED ENZYMATIC ACTIVITY

FIELD OF THE INVENTION

The present invention relates to a xylanase, and more particularly to a xylanase having improved enzymatic activity.

BACKGROUND OF THE INVENTION

Xylans are hemicelluloses, one of the major components in plant cell wall, and also the second most abundant polysaccharide on earth. Hence, the enzymes that degrade xylans can be widely applied in many different industries. Xylans are polysaccharides composed of many xylose units linked by β-1-4-glycosidic bond as their main backbones. Besides, xylans are complex and highly branched heteropolysaccharides which can be decorated by different side groups such as methyl group or acetyl group or other sugar molecules to form different structures of xylans. In addition, hemicellulose including xylan interacts with cellulose and lignin to constitute the tough plant cell wall. In nature, many kinds of herbivores and microbes need to degrade polysaccharides from plant cell wall into simple sugars as an energy source by different degrading enzymes including xylanase, cellulase and so on. In general, xylanolytic enzymes can be divided into several groups including endo-1,4-β-xylanase, β-xylosidase, acetylxylan esterase, arabinase and α-glucuronidase. Among these xylolytic enzymes, endo-1,4-xylanase is a key enzyme for degradation of xylan. Endo-1,4-xylanase (EC 3.2.1.8) is a glycoside hydrolase. It can degrade xylan to small fragments by hydrolysis of β-1,4-glycosidic bonds in the xylan backbone.

So far, the industrial applications of xylanases are widespread in feed industry, paper and pulp industry, food industry and textile industry, even in biofuel production. In general, xylanase needs to be suitable for different appropriate conditions according to various industrial needs. For example, acidic enzymes are suitable for the feed industry but paper and pulp industry prefers alkaline enzymes. In addition to the properties of enzymes, specific activity is also a key point of improving industrial enzymes. So, scientists in academic or industrial organizations devote to investigate better enzymes for different industrial needs by screening new genes in nature or modifying current enzymes. In general, there are two strategies of enzyme modification including directed evolution that randomly mutates the enzyme gene and selects with desirable properties or rationale engineering that specifically mutates the enzyme gene based on the structural information of the enzyme.

As previously mentioned, xylanases have been applied in many different industries. Besides of the suitable properties of enzyme, a good industrial xylanase also possesses the high enzymatic efficiency. Therefore, to increase specific activity of enzyme is also a key point for the improvement of industrial enzyme. Higher enzyme activity represents the cost down, and the companies will have better profit. Therefore, the present invention improves the enzyme activity by site-directed mutagenesis of the gene to reduce the cost of enzyme production and improves its economic value of industrial application.

SUMMARY OF THE INVENTION

An object of the present invention is to modify xylanase by means of structural analysis and site-directed mutagenesis to efficiently increase the enzyme activity, and improve its economic value of industrial application.

According to an aspect of the present invention, there is provided a xylanase having increased enzymaic activity. The xylanase has a modified amino acid sequence of SEQ ID NO: 2, wherein Tryptophan at position 125 is substituted with Phenylalanine and Phenylalanine at position 163 is substituted with Tryptophan.

In an embodiment, the amino acid sequence of SEQ ID NO: 2 is encoded by xynCDBFV gene isolated from *Neocallimastix patriciarum*.

In an embodiment, the xylanase has a full length amino acid sequence of SEQ ID NO: 8.

According to another aspect of the present invention, there is provided a xylanase having increased enzymaic activity. The xylanase has a modified a modified amino acid sequence of SEQ ID NO: 2, wherein Tryptophan at position 125 is substituted with Phenylalanine.

In an embodiment, the amino acid sequence of SEQ ID NO: 2 is encoded by xynCDBFV gene isolated from *Neocallimastix patriciarum*.

In an embodiment, the xylanase has a full length amino acid sequence of SEQ ID NO: 4.

According to a further aspect of the present invention, there is provided a xylanase having increased enzymaic activity. The xylanase has a modified a modified amino acid sequence of SEQ ID NO: 2, wherein Phenylalanine at position 163 is substituted with Tryptophan.

In an embodiment, the amino acid sequence of SEQ ID NO: 2 is encoded by xynCDBFV gene isolated from *Neocallimastix patriciarum*.

In an embodiment, the xylanase has a full length amino acid sequence of SEQ ID NO: 6.

According to an additional aspect of the present invention, there is provided an industrial use of the aforesaid xylanase, wherein the industrial use comprises uses in paper and pulp industry, feed industry, food industry, textile industry, and biofuel production.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the gene sequence and the amino acid sequence of the wild-type xynCDBFV;

FIG. 2 shows the protein structure of xynCDBFV in complex with oligosaccharide solved by X-ray crystallography;

FIG. 3 shows the sequences of the mutagenic primers;

FIG. 4 shows the gene sequence and the amino acid sequence of the W125F mutant;

FIG. 5 shows the gene sequence and the amino acid sequence of the F163W mutant;

FIG. 6 shows the gene sequence and the amino acid sequence of the W125F/F163W mutant.

DETAILED DESCRIPTION OF THE PREFERRED EMBODIMENT

Figure 7:
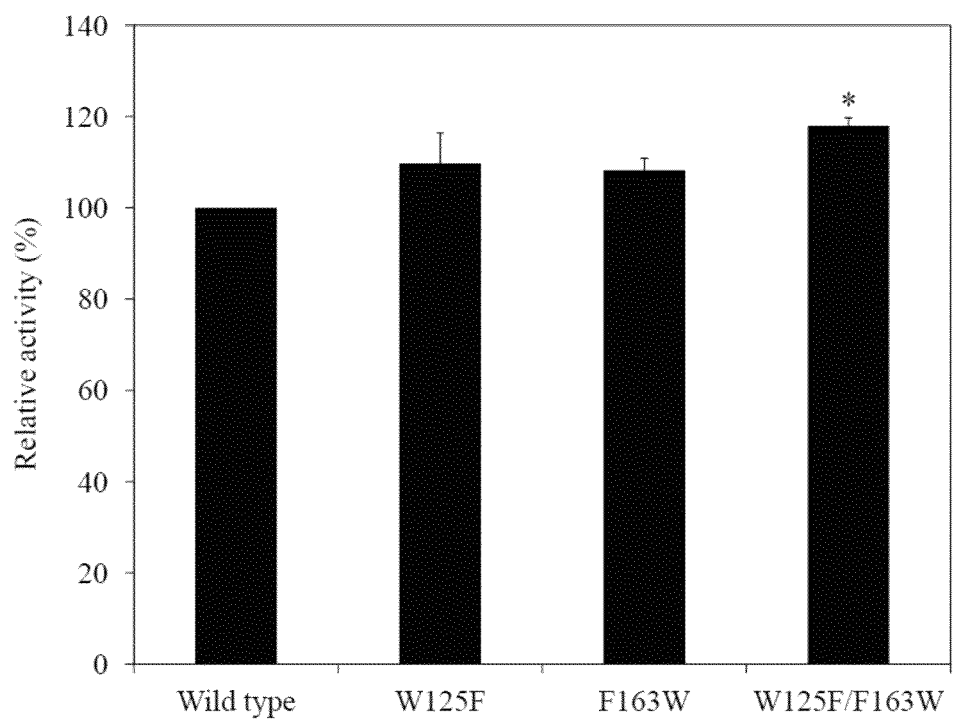
FIG. 7 shows the xylanase activity analysis of the wild-type and mutant xynCDBFV.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In the present invention, the xylanase, isolated from a rumen anaerobic fungus Neocallimastix patriciarum, was a mutated gene (xynCDBFV) by means of directed evolution and site-directed mutagenesis according to a previous study (Chen, Y. L., Tang, T. Y., and Cheng, K. J. (2001) Can J Microbiol 47, 1088-1094). As shown in FIG. 1, the full length of sequence of the xynCDBFV gene is 678 base pairs (SEQ ID NO: 1), which encodes a protein of 225 amino acids (SEQ ID NO: 2). In order to improve the industrial application value of this xylanase, its specific activity and catalytic efficiency were enhanced by site-directed mutagenesis based on the structural analysis.

Firstly, the xynCDBFV gene was constructed into pPIC-ZαA vector by EcoRI and NotI. The plasmid DNA was linearized by PmeI and transformed into Pichia pastoris. The transformants were selected on YPD plates containing 100 μg/ml Zeocin and cultured at 30° C. for 2 days. The protein expression of transformed gene was tested by the following small-scale expression. The selected colonies were separately inoculated in 5 ml YPD and then amplified in 50 ml BMGY at 30° C. for 24 hr. The cells were harvested and then resuspended in 20 ml BMMY containing 0.5% methanol to induce protein expression. After that, the transformant with higher expression level was chosen for the following scale-up expression. The cells were inoculated in 5 ml YPD and then amplified in 500 ml BMGY at 30° C. for 24 hr. The cells were harvested and then resuspended in 250 ml BMMY to induce protein expression at 30° C. for 2 days. The supernatant was collected by centrifugation and then dialyzed twice against 5 L of buffer containing 25 mM Tris, pH 7.5 for following purification. The proteins were purified by FPLC system using DEAE column. The purified proteins were finally concentrated to 10 mg/ml in 25 mM Tris, pH 7.5; 150 mM NaCl, and then stored at −80° C.

To solve the protein structure of xynCDBFV by X-ray crystallography, the protein crystal was obtained by using sitting drop vapor diffusion method at room temperature. The crystal was firstly screened by crystal screen kits and the better crystal was obtained by a condition composed of 2 M Ammonium sulfate and 0.1 M Tris, pH 8.5 at room temperature for 2 days. The phase problem was solved by molecular replacement method. Furthermore, the protein structures of xynCDBFV in complex with xylobiose or xylotetraose were determined by soaking the crystals with these two oligosaccharides having a concentration of 10 mM, respectively.

FIG. 2 shows the protein structure of xynCDBFV in complex with oligosaccharide solved by X-ray crystallography. According to the structure shown in FIG. 2, it is observed that Trp125 and Phe163 have interaction with oligosaccharide in the active site and considered these two residues may be important to the catalytic reaction of xynCDBFV. So, Trp125 and Phe163 were selected for site-directed mutagenesis.

The mutants of xynCDBFV including W125F, F163W and W125F/F163W were obtained by site-directed mutagenesis. Firstly, the mutated genes were individually acquired by PCR method, and the sequences of primers for these mutants were listed in FIG. 3, wherein W125F means Tryptophan at position 125 was mutated into Phenylalanine, and F163W means Phenylalanine at position 163 was mutated into Tryptophan. The original template was then removed by DpnI. After that, the mutated genes were separately transformed into E. coli and the mutations were confirmed by DNA sequencing. Finally, the mutated genes were individually transformed into P. pastoris as previously mentioned.

FIGS. 4 to 6 show the gene sequence and amino acid sequence of W125F, F163W and W125F/F163W mutants, respectively, wherein W125F means Tryptophan at position 125 was mutated into Phenylalanine, and F163W means Phenylalanine at position 163 was mutated into Tryptophan, and W125F/F163W is a double mutant in which Tryptophan at position 125 was mutated into Phenylalanine and Phenylalanine at position 163 was mutated into Tryptophan. The gene sequences of W125F, F163W and W125F/F163W mutants were numbered as SEQ ID NO: 3, SEQ ID NO: 5, SEQ ID NO: 7, and the amino acid sequences of W125F, F163W and W125F/F163W mutants were numbered as SEQ ID NO: 4, SEQ ID NO: 6, SEQ ID NO: 8, respectively.

To verify the difference between the wild-type and mutant xynCDBFV, the xylanase activity assay was further performed. The xylanase activity assay was modified from a previous study and performed as follows. In general, the proper concentration of protein solution was mixed with 1% β-xylan substrate in the proportion of 1 to 9 and incubated at 55° C. for 10 min. The mixed solution was added with 1 fold volume of 1% DNS solution and then incubated at 100° C. boiled water for 10 min. The solution was finally added with 2.5 fold volume of ddH$_2$O. The absorption of OD540 was detected and the enzyme activity was obtained. The standard curve of enzyme activity was determined by 0-0.6 mg/ml xylose standard solution. One unit was defined as the enzyme level that could release 1 μmole product per minute.

FIG. 7 shows the xylanase activity analysis of the wild-type and mutant xynCDBFV. The xylanase activity of the wild type enzyme was set to 100%. The standard error of the mean (SEM) was also shown here. Two-tailed P values were determined by an unpaired Student's t-test, and when $P<0.05$, it is determined there is a significant difference (*). From the results shown in FIG. 7, it is observed that the specific activities (unit/mg) of W125F, F163W and W125F/F163W mutants were all higher than the wild type. Especially, W125F/F163W mutant significantly increased in the specific activity of 20% when compared to the wild type. Besides, the expression levels of the wild-type enzyme and W125F/F163W mutant were similar to each other. So, the total xylanase activity of W125F/F163W was also higher than the wild type. That means W125F/F163W mutant has higher potential of industrial application than that of wild type.

In conclusion, in order to improve the enzymatic activity of xynCDBFV, the present invention solved the protein structure of xynCDBFV by X-ray crystallography, and Trp125 and Phe163 located in the active site of the enzyme were selected for site-directed mutagenesis. According to the xylanase activity analysis, the specific activities of W125F, F163W and W125F/F163W mutants were all higher than the wild-type protein, so the production cost can be reduced and the economic value of industrial application can be increased.

Moreover, the application fields of xylanases in industry are widespread, such as paper and pulp industry, feed industry, food industry, textile industry, biofuel production and so on. For the juice production in food industry, the degradation of pectin which largely existed in fruits is crucial while it is often interfered by other polysaccharides like hemicellulose co-existed with the pectin. Therefore, xylanase can be added with pectinase to help the fruit degradation and further improves juice clarification in the juice production process. Besides, xylanase can efficiently assist to degrade raw materials like barley or wheat in the saccharification step of brewing industry and further reduce the viscosity. For feed industry, liquid xylanase can be spurted on bran carriers and mixed with feed to help animals degrading feed materials and improve the digestion and absorption of carbohydrate in animal bowels. As for textile industry, xylanase can be applied in the retting of flax, hemp and so on to reduce or replace traditional chemical retting method. In addition, industrial xylanase is also important to the paper and pulp industry, especially the pulp bleaching process. Xalanase can efficiently remove the residual lignin with brown color by degradation of hemicellulose which has tightly interaction with lignin and further reach to the result of bleaching. So, xylanase can replace chlorine dioxide which is used in the traditional bleaching method and further reduce the toxic byproducts. As for biofuel industry, xylanase can efficiently assist to degrade plant materials to simple sugars in the saccharification process. Then, the fermenting microbes can utilize simple sugars by fermentation to produce bioethanol. Thus, xylanase can be widely applied in many industries and has high application value.

In the present invention, the W125F, F163W and W125F/F163W mutants of xynCDBFV enhanced the specific activity of xylanase by genetic engineering to reduce the production cost and further improve the economic value of industrial application. Therefore, the present invention successfully modified xynCDBFV to improve the enzymatic activity thereof, and thus, the present invention possesses high industrial value.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A xylanase comprising a modified amino acid sequence of SEQ ID NO: 2, wherein Tryptophan at position 125 is substituted with Phenylalanine and Phenylalanine at position 163 is substituted with Tryptophan.

2. The xylanase according to claim 1 wherein the amino acid sequence of SEQ ID NO: 2 is encoded by xynCDBFV gene isolated from *Neocallimastix patriciarum*.

3. The xylanase according to claim 1 having a full length amino acid sequence of SEQ ID NO: 8.

4. A xylanase comprising a modified amino acid sequence of SEQ ID NO: 2, wherein Tryptophan at position 125 is substituted with Phenylalanine.

5. The xylanase according to claim 4 wherein the amino acid sequence of SEQ ID NO: 2 is encoded by xynCDBFV gene isolated from *Neocallimastix patriciarum*.

6. The xylanase according to claim 4 having a full length amino acid sequence of SEQ ID NO: 4.

7. A xylanase comprising a modified amino acid sequence of SEQ ID NO: 2, wherein Phenylalanine at position 163 is substituted with Tryptophan.

8. The xylanase according to claim 7 wherein the amino acid sequence of SEQ ID NO: 2 is encoded by xynCDBFV gene isolated from *Neocallimastix patriciarum*.

9. The xylanase according to claim 7 having a full length amino acid sequence of SEQ ID NO: 6.

10. An industrial use of the xylanase according to claim 1, wherein the industrial use comprises uses in paper and pulp industry, feed industry, food industry, textile industry, and biofuel production.

* * * * *